(12) United States Patent
Fishbine et al.

(10) Patent No.: US 9,255,900 B2
(45) Date of Patent: Feb. 9, 2016

(54) HAND HELD TOXICITY TESTER

(71) Applicants: Glenn M. Fishbine, Montgomery, MN (US); Nancy DeGidio, Montgomery, MN (US); Arnie W. Kwong, Saint Paul, MN (US)

(72) Inventors: Glenn M. Fishbine, Montgomery, MN (US); Nancy DeGidio, Montgomery, MN (US); Arnie W. Kwong, Saint Paul, MN (US)

( * ) Notice: Subject to any disclaimer, the term of this patent is extended or adjusted under 35 U.S.C. 154(b) by 0 days.

(21) Appl. No.: 13/847,306

(22) Filed: Mar. 19, 2013

(65) Prior Publication Data

US 2014/0176940 A1 Jun. 26, 2014

Related U.S. Application Data

(60) Provisional application No. 61/612,418, filed on Mar. 19, 2012.

(51) Int. Cl.

| | |
|---|---|
| *G01N 21/27* | (2006.01) |
| *G01N 23/223* | (2006.01) |
| *G01N 21/71* | (2006.01) |
| *G01J 3/02* | (2006.01) |
| *G01N 21/55* | (2014.01) |
| *G01N 21/65* | (2006.01) |

(52) U.S. Cl.
CPC .............. *G01N 23/223* (2013.01); *G01J 3/0218* (2013.01); *G01N 21/55* (2013.01); *G01N 21/65* (2013.01); *G01N 21/718* (2013.01); *G01N 2201/0221* (2013.01); *G01N 2223/076* (2013.01)

(58) Field of Classification Search
CPC ......... G01N 21/65; G01N 21/658; G01J 3/44; G01J 3/02; G01J 3/2823
USPC .......................................... 356/301, 300, 318
See application file for complete search history.

(56) References Cited

U.S. PATENT DOCUMENTS

| | | | | |
|---|---|---|---|---|
| 7,557,917 | B1 * | 7/2009 | Beesley ......................... | 356/318 |
| 2008/0100835 | A1 * | 5/2008 | Ban et al. ....................... | 356/301 |
| 2008/0123095 | A1 * | 5/2008 | Hubner et al. ................. | 356/328 |
| 2009/0290151 | A1 * | 11/2009 | Agrawal et al. ................ | 356/318 |
| 2010/0264820 | A1 * | 10/2010 | Sumitomo et al. ............. | 313/639 |
| 2012/0217422 | A1 * | 8/2012 | Yabu et al. ................ | 250/504 R |
| 2013/0155027 | A1 * | 6/2013 | Holmgren et al. ............. | 345/175 |

OTHER PUBLICATIONS http://en.wikipedia.org/wiki/Partial_least_squares_regression.*

* cited by examiner

*Primary Examiner* — Tarifur Chowdhury
*Assistant Examiner* — Mohamed K Amara
(74) *Attorney, Agent, or Firm* — Pepper Hamilton LLP

(57) ABSTRACT

A system and method for reliably testing for toxic substances is described. Based on spectrographic means, the system embodies one or more types of spectrometers, designed for the detection of toxic elements such as lead, and alternatively designed for the detection of toxic compounds such as asbestos. By restricting the broad functionality common to a typical spectrometer, dramatic cost reductions can be made permitting the device to be cost-effectively manufactured and made available to the typical consumer. The device can be portable and incorporates safety systems to inhibit improper use.

26 Claims, 17 Drawing Sheets

Figure 1: Exemplary hand held device
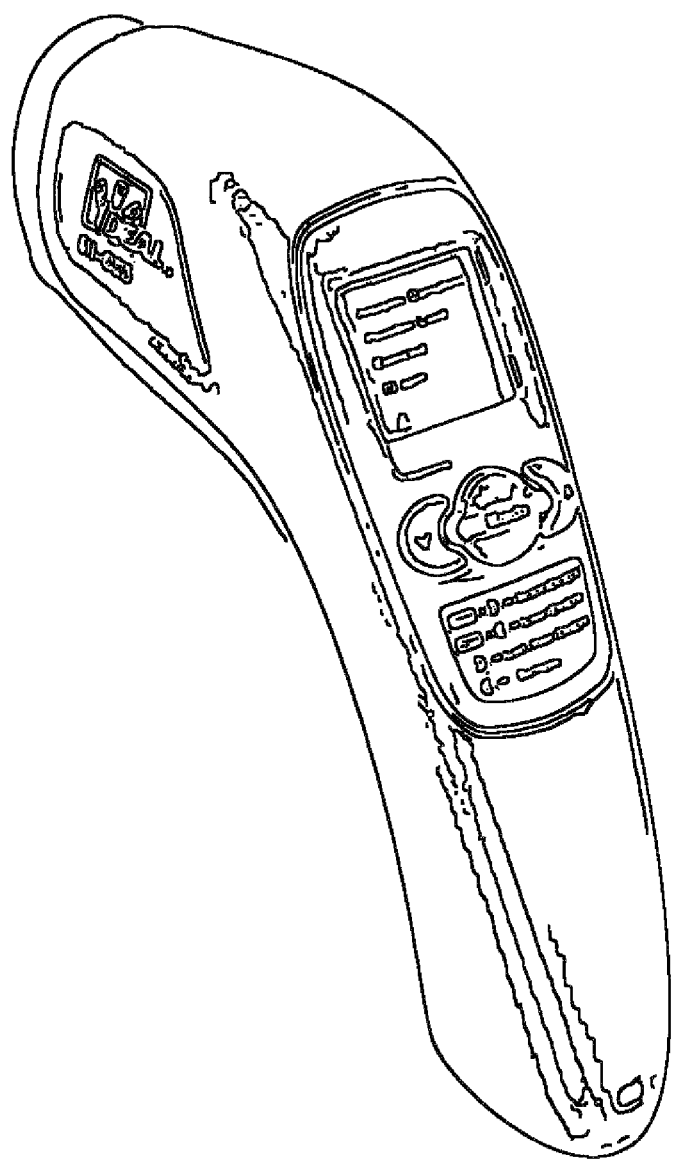

Figure 2: The internal function of the device
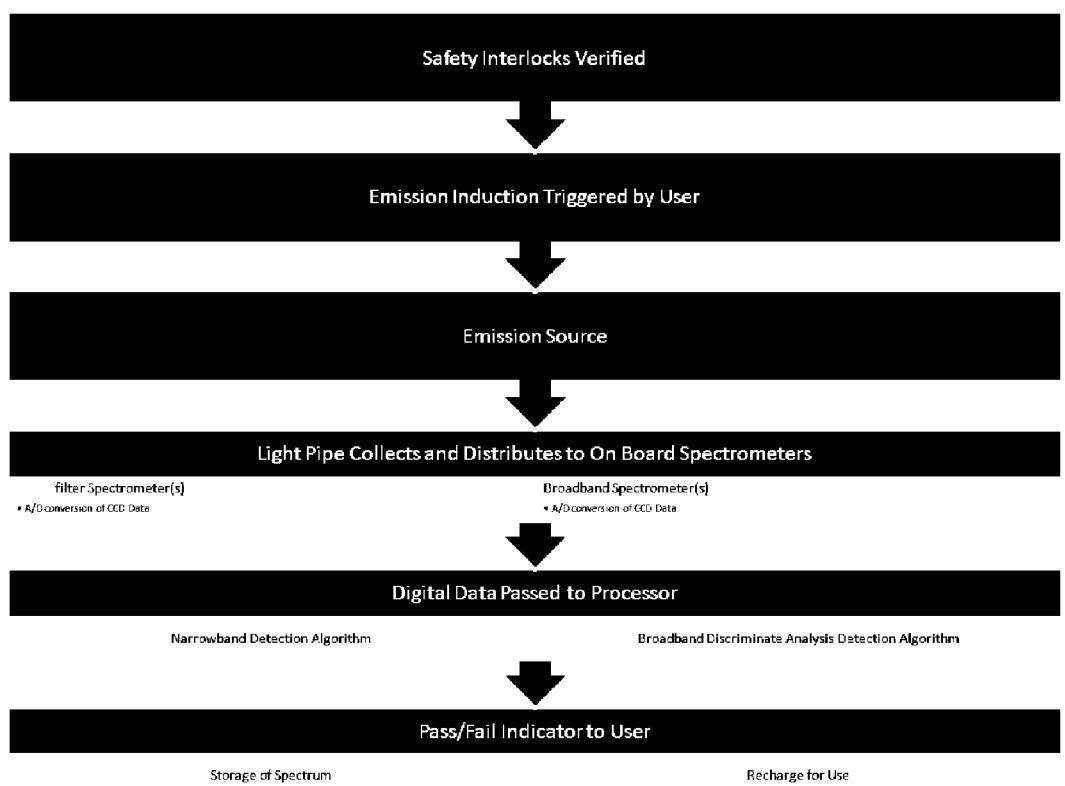

Figure 3: An exemplary spectroscopy subsystem of the device
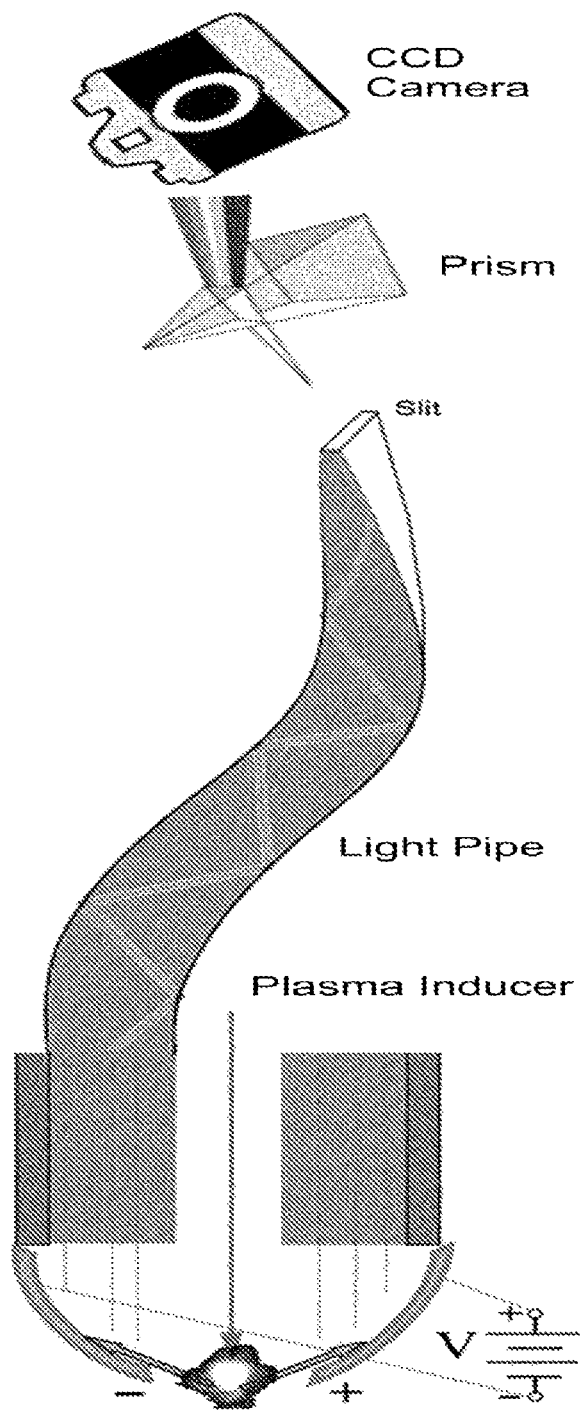

Figure 4: An exemplary bandpass filter for detecting lead (PB)
Exemplary Bandpass Filter
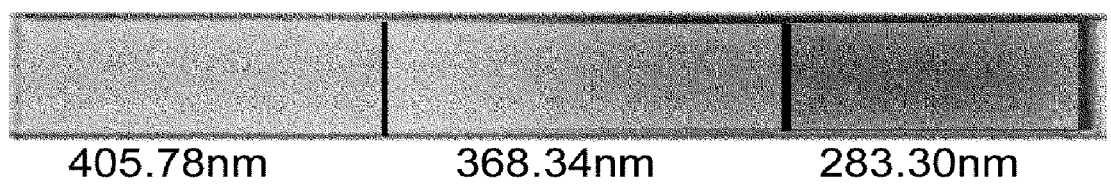
405.78nm      368.34nm      283.30nm Figure 5: A bandpass filter structure for one CCD
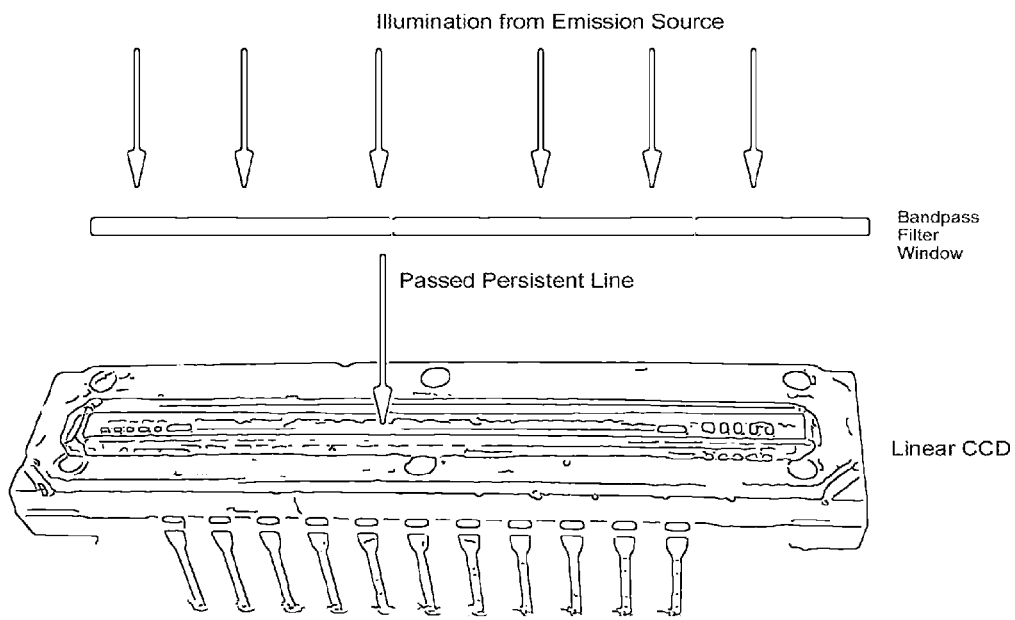
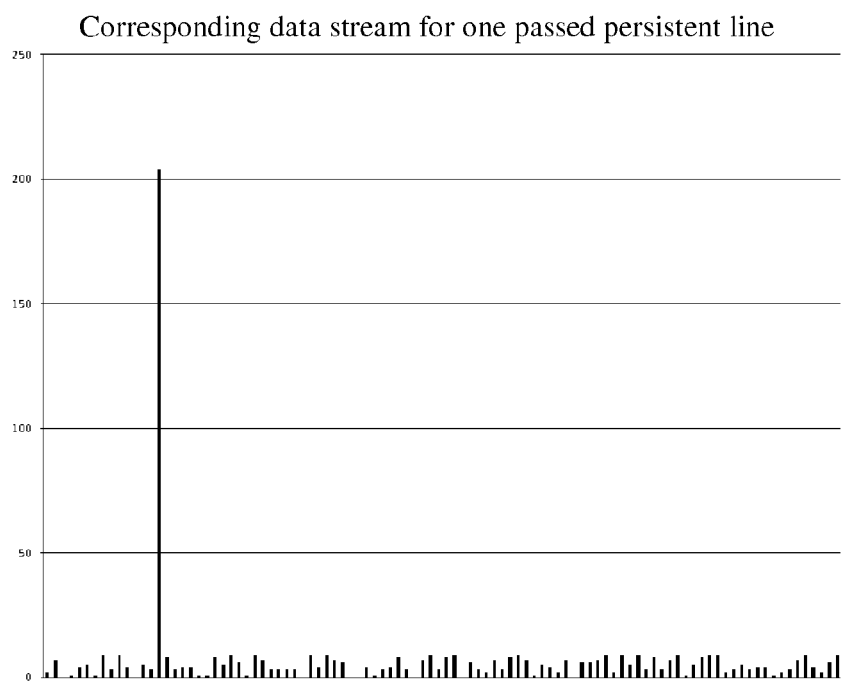
Corresponding data stream for one passed persistent line The principle of total internal reflection

HAND HELD TOXICITY TESTER

RELATED APPLICATION

This application claims priority to U.S. Provisional Patent Application No. 61/612,418, filed on Mar. 19, 2012, which is incorporated by reference herein.

FIELD

This description relates generally to a system, and method for detecting toxic substances.

BACKGROUND

The prevalence of toxic substances in the environment has resulted in increasing regulation and control of producers of toxic materials and their use. Upwards of 50,000 chemicals are routinely introduced into the environment, the majority of which have not been tested for safety. A much smaller number of known toxic chemicals are common in the environment and pose known real hazards for individuals. Testing technologies that permit individuals to determine the safety of their immediate environment are too expensive for consumer use or relatively unreliable or focused on the detection of single substances.

BRIEF SUMMARY

Here we describe a device, system and method for reliably testing for a multiplicity of toxic substances. Based on spectrographic means, the system can be deployed incorporating one or several types of spectrometers, including a system where two types are embedded, one designed for the detection of toxic elements such as lead, and the other designed for the detection of toxic compounds such as asbestos. By restricting the broad functionality common to a typical spectrometer, dramatic cost reductions can be made permitting the device to be cost-effectively manufactured and made available to the typical consumer.

Apparatus, systems and methods that permit the portable and rapid detection of a wide range of toxic substances are disclosed. The system is a handheld multi-mode spectrometer which incorporates a spectroscopic system such as a low powered laser induced breakdown spectrometer (LIBS) design or other emission or absorption inducing approaches such as sliding spark spectroscopy (SSS) or laser ablation emission spectroscopy (LAES). Light from the sampled target is directed to one or more spectrometers. In one spectrometer type, the light is directed to a conventional charge coupled device (CCD), or any other device that collects and provides measurements of electromagnetic energy, that has been masked with a pattern of one or more discrete narrow band bandpass filters which pass light only at wavelengths specific to individual elements of concern, such as lead, cadmium, etc. In another type, the light is presented through a conventional spectrometer design which permits broad spectrum detection at a resolution which permits broad peak molecular detection to occur.

The output from the CCD(s) or other electromagnetic measurement device is digitized and presented to an onboard logic circuit or microprocessor which utilizes conventional rewritable/reprogrammable memory which retains the system boot loader, software for the analysis of the spectrum and access to a library of specific detection algorithms tailored to substances of interest. The resulting spectra can be stored in the memory device, and an indicator is provided to the operator regarding the presence or absence of toxic substances, inclusive of toxic elements, compounds, chemical or biological hazards The system further can be designed to be modular such that the spectrometer section can be replaced with an alternate spectrometer module. A module being a plug-and-play compatible spectrometer which can deliver a spectrum to the balance of the device for analysis, said module being interchangeable with other modules employing alternative spectroscopic means. This permits specialized detection means to be employed, for example, by substituting a different spectrographic method, i.e. Raman spectroscopy instead of LIBS, or a different set of bandpass filters targeted to a different set of elements of interest. Further the modularity permits the plug-in substitution of an alternative spectrometer that may have other desirable properties such as a higher cost higher resolution broadband spectrometer.

Additional features and advantages of the invention will be made apparent from the following detailed description of illustrative embodiments that proceeds with reference to the accompanying drawings.

BRIEF DESCRIPTION OF THE DRAWINGS

FIG. 1 is a drawing showing an exemplary hand held device in accordance with an embodiment of the invention;

FIG. 2 is a drawing showing the internal function of an exemplary device;

FIG. 3 is a drawing showing an exemplary spectroscopy subsystem of the device;

FIG. 4 is a drawing showing an exemplary bandpass filter for detecting lead (PB) for use in some embodiments;

FIG. 5 is a drawing showing a bandpass filter structure for one CCD;

DETAILED DESCRIPTION OF ILLUSTRATIVE EMBODIMENTS

Figure 6:
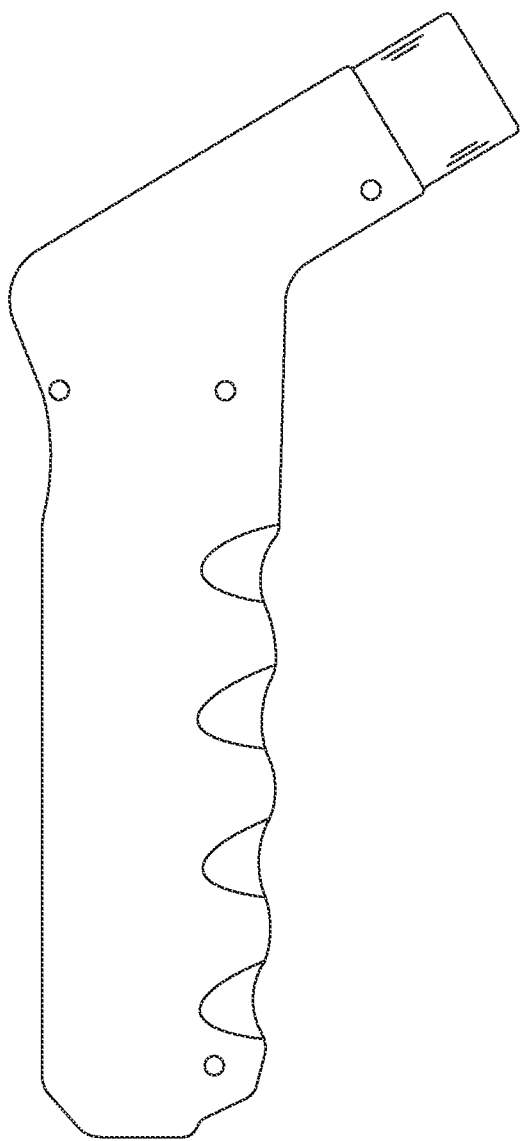
FIG. 6 is a drawing showing an exemplary sampling head for use in some embodiments.

Exemplary methods and systems are disclosed for a toxicity tester that incorporates one or more spectrographic approaches which expand the range of possible toxicity tests yet which permits a simple pass/fail indicator to the operator. In some embodiments, the toxicity tester may be packaged for use as a portable unit. In some embodiments, the toxicity tester may be packaged for use as a laboratory unit.

The detection of toxic content in toys and home settings, for example, can be accomplished with a suite of different test procedures. In a typical scenario, suspect samples are provided to a certified laboratory which can apply a variety of tests inclusive of chemical analysis, emission and absorption spectroscopy, mass spectroscopy, Raman spectroscopy, and other established means. Typically, the approach is one of looking for the presence or absence of a single substance of concern, such as lead, and measuring the presence, for example, in parts per million.

Several field portable devices have been developed which typically use x-ray fluorescence spectroscopy and are capable of a wide range of tests. However, these devices emit x-rays and hazardous materials ("HAZMAT") training is required prior to use to avoid accidental exposure for x-rays. These devices, while effective, are unsuited for consumer use. Furthermore, their costs tend to be in the $15,000 to $25,000 range, many with additional operating costs, which excludes most consumers from acquiring these devices.

Field portable devices utilizing laser induced breakdown spectroscopy (LIBS) and sliding spark spectroscopy (SSS) have been developed which permit sampling of materials in contact or from a standoff distance of several meters. However, LIBS units have extremely high-powered lasers which require extreme caution in use and have larger price tags comparable to that of luxury cars. Further, the techniques employed, while relatively non-destructive to the sample, employ power levels which cannot be licensed for general consumer use in many jurisdictions.

U.S. Pat. No. 7,236,243 defines a hand-held portable spectrometer which utilizes absorption spectra to identify materials. The device includes a removable head which enables selection of different types of spectroscopic methods.

U.S. Pat. No. 7,791,027 discloses a hand-held portable spectrometer which uses a MEMS device to create filter means of infra-red emissions to dynamically select the spectra of interest.

U.S. Pat. No. 5,319,437 discloses a hand-held portable infra-red spectrometer which can operate in either a reflectance spectroscopy mode or a radiometric spectroscopy mode. It further employs a replaceable memory for both software and spectra replacement.

U.S. Pat. No. 6,031,233 discloses a hand-held portable infra-red spectrometer which incorporates an acoustically tunable filter to dynamically select the spectra of interest.

U.S. Pat. No. 4,678,332 discloses a fiber optic means of transporting spectroscopic information from the illumination source to the spectrometer.

U.S. Pat. No. 7,339,668 discloses a light pipe means of transporting spectroscopic information from the illumination source to the spectrometer.

U.S. Pat. No. 7,412,129 discloses a fiber optic system used to transport light from a laser induced breakdown spark to a spectroscopic system.

The prior art does not, however, reveal a device specifically designed to detect and report toxic substances of interest, as described herein and exemplified in the figures.

In embodiments of the invention, we focus on the detection of toxic hazards common in the environment. Based, for example, on the list published by the Comprehensive Environmental Response, Compensation, and Liability Act, (CERCLA list) which details environmental substances of high concern, we incorporate means of detection of materials from a defined list of materials of interest. For example, rather than performing a broad band spectral analysis common to most types of spectroscopy, we employ means of detecting specific elements and compounds which permit a toxicity indication to be reported by the instrument.

In one embodiment, the first stage of the system includes a modular LIBS system which is placed on the item of interest. Under user control, a "trigger" is activated which fires the laser resulting in the LIBS plume, which is available for emission based spectral analysis. The light from the plume is directed in one or more directions each of which is directed to a spectrometer design for a narrow range of sensitivities. For example, by directing light to a CCD, such as a Toshiba TCD1705DG, which has been overlaid with a small set of optical bandpass filters, such as the Semrock BrightLine® Quad-Band bandpass filters, or an arrayed waveguide grating (e.g., a transport mechanism from filter), or other bandpass filter means, CCD pixels under each filter will record light emissions at a very narrow spectral region. For example, if three regions on the CCD are masked with bandpass filters, each of which passes light at respectively 405.78, 368.34, and 283.30 nanometers, then we have a system which looks specifically at the most intense persistent spectral lines associated with the element lead (PB). If we similarly examine the CCD voltages under each masked region for the relative respective intensities of 1000, 400 and 300, then we derive a positive indication of the presence of lead in the sample. Such indication, or determination of the presensese of, in this example, lead, can be made by something as simple as a non-zero voltage reading, or by other methods including those as complex as a statistical analysis of multiple signals at different wavelengths or harmonics, depending upon the spectrographic means employed, and the detection method appropriate for that material. In the case of emission spectroscopy, the actual intensity of the signal derived from the CCD regions can in turn be an indicator of how many parts per million are in the sample. Thereby, we can derive a toxicity measurement for lead. The same filter approach can be applied using a Sliding Spark or even a simple flame (LAES) emission spectrograph. Any spectrographic means may be employed insofar as the means provides a specific measurable wavelength or wavelengths of photonic or harmonic properties which can be representative of the elemental, chemical, or other signatures of toxic elements, compounds, chemicals or biohazards. An example of the internal functioning of the device is shown in FIG. 2.

Similarly, an identical approach can be used to detect absorption spectra. For example, if the filters are tuned around the mercury absorption line at 253.65, the absence of a drop off would be indicative of the absence of mercury while the existence of a drop off in comparison to adjacent wavelengths would be indicative of the presence of mercury.

Using the CERCLA list example, triplets of bandpass filters can be overlaid on the CCD which permits the detection of some of the elements on the CERCLA list:

ACTINIUM-227
ALUMINUM
AMERICIUM
AMERICIUM-241
ANTIMONY
ARSENIC
BARIUM
BERYLLIUM
BROMINE
CADMIUM
CESIUM-137
CHLORINE
CHROMIUM
CHROMIUM(VI) OXIDE
CHROMIUM, HEXAVALENT

COBALT
COPPER
FLUORINE
IODINE-129
IODINE-131
LEAD
LEAD-210
MANGANESE
MERCURY
NICKEL
PALLADIUM
PHOSPHORUS, WHITE
PLUTONIUM
POLONIUM-210
POTASSIUM-40
SELENIUM
SILVER
VANADIUM
ZINC

These 34 elements can in principle detected with approximately 100 optical bandpass filters which overlay a linear CCD of approximately 5,000 elements permitting approximately 50 pixel regions of light gathering capacity for each persistent line of interest. Addition or deletion of other elements of interest can readily be accommodated by adding or deleting bandpass filter windows. Selection of three persistent lines is an arbitrary choice and more or fewer lines can be selected based upon the desired sensitivity for a given atomic species. Once the CCD has accumulated the light, the results can be digitized through conventional analog to digital conversion means, such as an EXAR XRD98L61, and the digital data can be presented to a microprocessor, such as a Texas Instruments TMS320C2810, which executes a software program that algorithmically determines the presence or absence of a particular element by looking at the pixels associated with that element's persistent lines, the relative intensity at those lines, and the overall intensity. Through this means, we can have a broad toxicity test performed very rapidly and can provide the system operator with a pass/fail or ppm indication for toxic elements of interest.

In cases where broad spectra such as Iron or Tungsten may be present, the system can avoid washout effects and false positives, by adding additional bandpass filters on either side of the persistent lines to ensure that the drop-off confirms the presence of a particular atomic species. For example, the confirmation of lead could be supported by having filters at 405.78 nanometers where lead is expected, and 405.68 and 405.88 nanometers where it is not. Detection at 405.78 nanometers coupled with no detection at 405.68 and 405.88 would be a good confirmation while an equal detection at all three would be indicative of some other broad emission effect perhaps unassociated with lead. In cases such as lead, a single filter at 405.78 can be selected as the sole means of detection in the absence of adjacent filters. An example of such a filter is shown in FIG. 5.

In a simple embodiment where the target is, for example, Lead, which has a primary emission at 406.78 nanometers, the primary bandpass filter can be set for that frequency and adjacent bandpass filters can be optionally incorporated to avoid confounding detections of for example, mercury, iron or tungsten.

In the case where LIBS is not the preferred spectroscopy means, alternative means such as SSS, LAES, Raman, XRF, reflectance or other means can be employed utilizing the same detection method described above. As example of a spectroscopy module is shown in FIG. 4.

In one embodiment, a sliding spark is generated with a 5 mm separation between heads and a 10 kv discharge initiates the spark. Emission is directed either directly into the spectrometer or, in the case where a single emission line is filtered, directed via a fiber optic feed on to a bandpass filter such as a Spectro-Film P/N 405.7 nm filter which sits in front of a photodetector. A photodetector adjacent to the contact point between the fiber optic and the filter can detect ambient light levels derived from the discharge and provided real-time illumination calibration data to support the software in determining the ppm content of the sample. In one embodiment, a PIC 16f688 microprocessor from MicroChip Technology, Inc. was able to derive an SSN spectrum over a period of 8 microseconds and generate the pass/fail signal in under a total of 10 microseconds after detection of the spark discharge.

The detection of complex molecular compounds of toxic materials such as asbestos can be handled by a similar approach. For example, one species of asbestos, Chrysotile which is molecularly $Mg_3(Si_2O_5)(OH)_4$ could be detected by a family of filters looking at Magnesium, Silicon, Oxygen and Hydrogen.

An alternate approach is envisioned as part of one embodiment. A more conventional spectrometer at much lower resolution than that provided by the optical bandpass filters is also included. In this case, a conventional prism or diffraction grating may be employed which delivers a broad spectrum to a second CCD, such as a Toshiba TCD1705DG, or for higher resolution, partial overlapping or non-overlapping spectra are provided to two or more CCDs. In this case, the intent is to detect complex molecular signatures based on relative band height positions. For example, FIG. 5 describes a spectrometer design which may select more than a few wavelengths. For example, a 4,096 element CCD can in principle discriminate between 4,096 discrete wavelengths of interest. The degree of discrimination in an exemplary optical spectrometer is limited only by the choice of CCD and the number of pixels embedded, coupled with the optical meanse of separating wavelengths at the scale of the CCD. Whether fine or course measurements are used is relevant insofar as precise measurements beyond "present"/"not present" are required.

Partial Least Squares Discriminate Function Analysis (PLDA), such as that available from The Royal Statistical Society's publications and implementations via StatLib, and related methods have been utilized to quantitatively identify complex molecular items such as various types of explosives, chemical weapons, and even bacteria. In this context, spectra are assumed to be "severely overlapping" that is, there are multiple overlapping emissions from multiple complex molecules in the sample spectrum. A typical identification approach practiced in the industry is to develop a reference library of finite impulse response matrix digital filters ("FIRMDF") for each toxic compound of interest. The PLDA method essentially contains a catalog of filters which is reduced to a set of equations that are parameterized by different emission levels in the measured spectrum. When the spectrum is processed by the PLDA a probability is given that the spectrum is derived from a particular source. Utilizing this method, complex identifications can be made with relative ease even if the input spectrum data is of comparatively low resolution, i.e., line width discrimination in the multi nanometer range rather than tenth or hundredth nanometer.

Using this approach a relatively low resolution CCD can be utilized, such as a Toshiba TCD1705DG, which will deliver spectral results after conversion from analog to digital form to the microprocessor on which a PLDA categorization algorithm generates classification scores for the spectrum and delivers a probability of detection and detection level for each toxic compound for which it has a resident FIRMDF.

Where high precision is required, a portion of the available spectrum can be selected for high resolution by using an appropriate prism or diffraction grating that spreads the spectrum over the CCD area in a narrow range of interest. In this way, resolutions for the desired range can be selected from several nanometers resolution to fractions of a nanometer.

In one embodiment, the operating system, detection algorithms and detection data are stored on a removable memory device such as a Kingston SDC/2 GB micro SD card. This permits the software library to be updated as better detection algorithms become available. This also permits additional toxic substances to be added to the repertoire. It further permits collected spectra to be recorded and analyzed separately or uploaded to a central data base for other purposes.

Figure 7A:
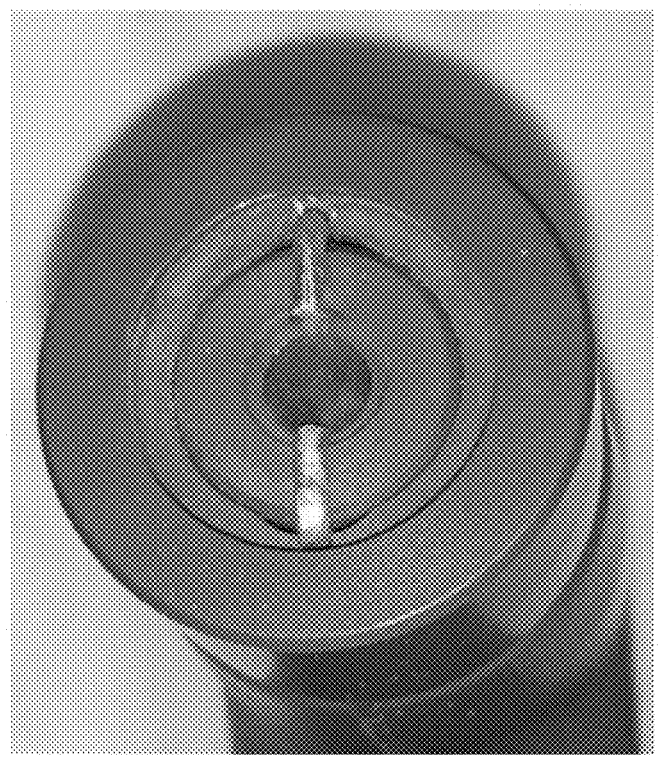
FIGS. 7A and 7B depict an end view and a perspective view, respectively, of an exemplary sample point using SSS.
Figure 7B:
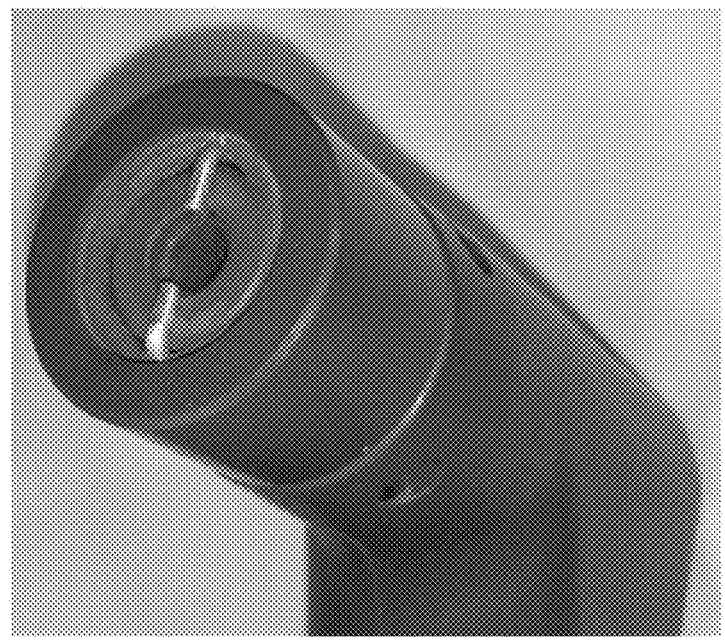
Figure 8:
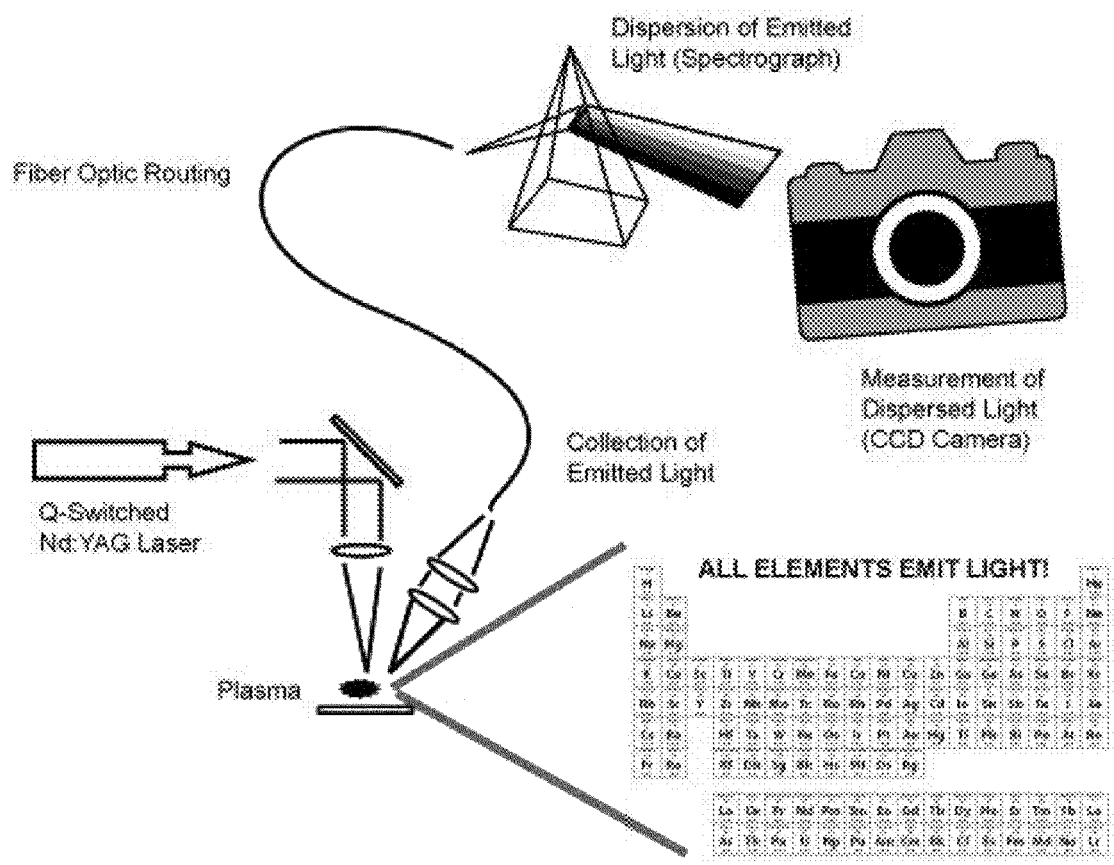
FIG. 8 is a drawing showing an exemplary Laser Induced Breakdown Spectroscope for use in some embodiments.
Figure 9:
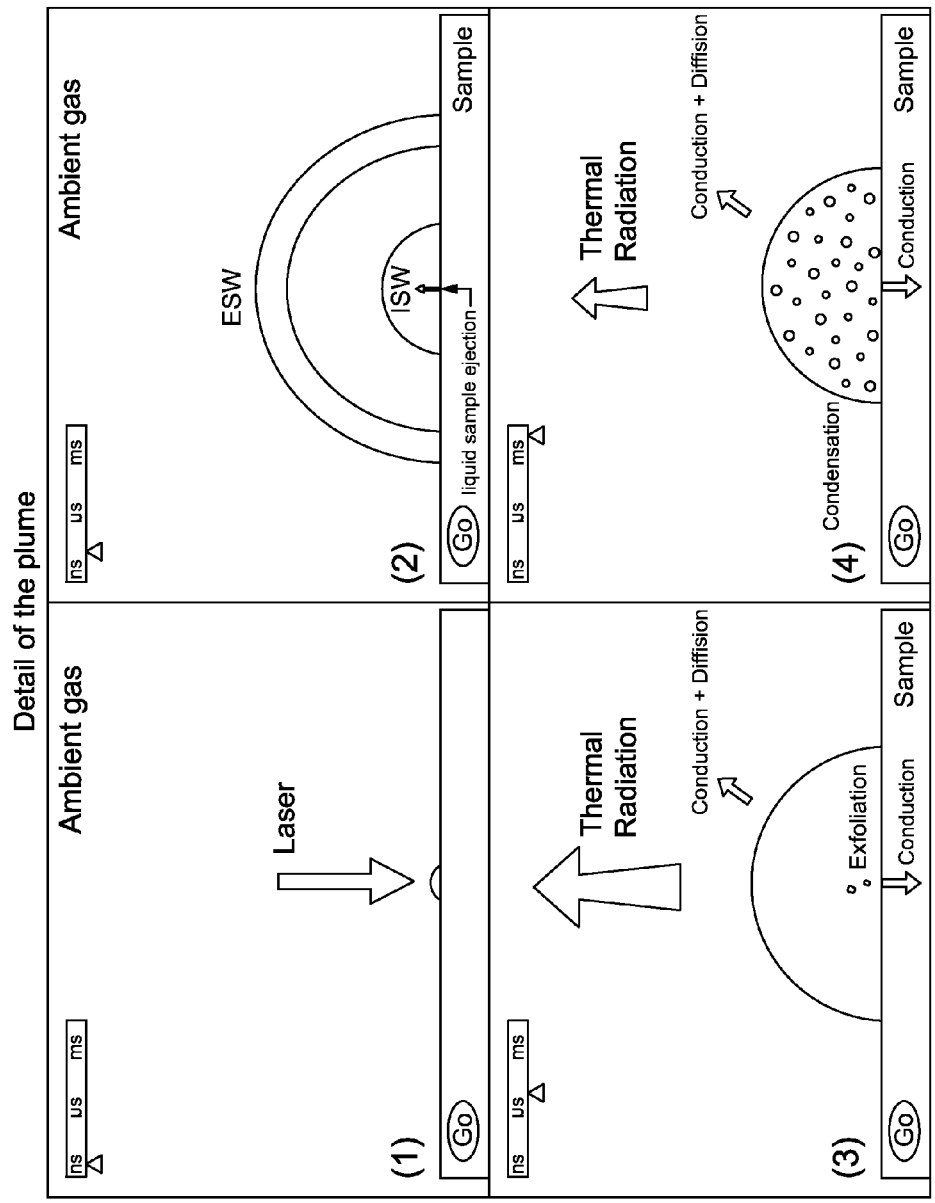
FIG. 9 is a drawing showing detail of an exemplary plume.
Figure 10:
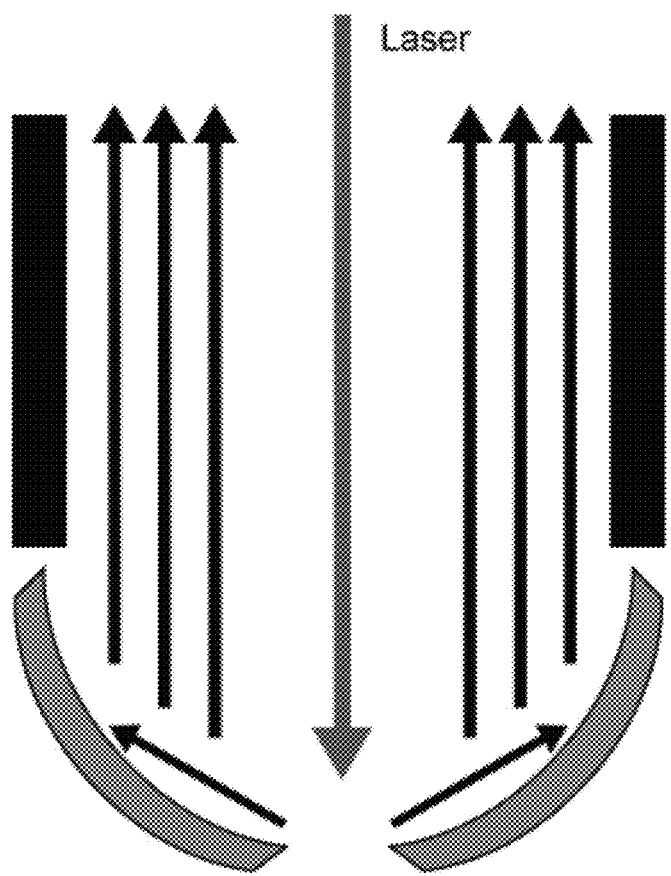
FIG. 10 is a drawing an exemplary tip which captures more available light for use in some embodiments of the invention.
Figure 11:
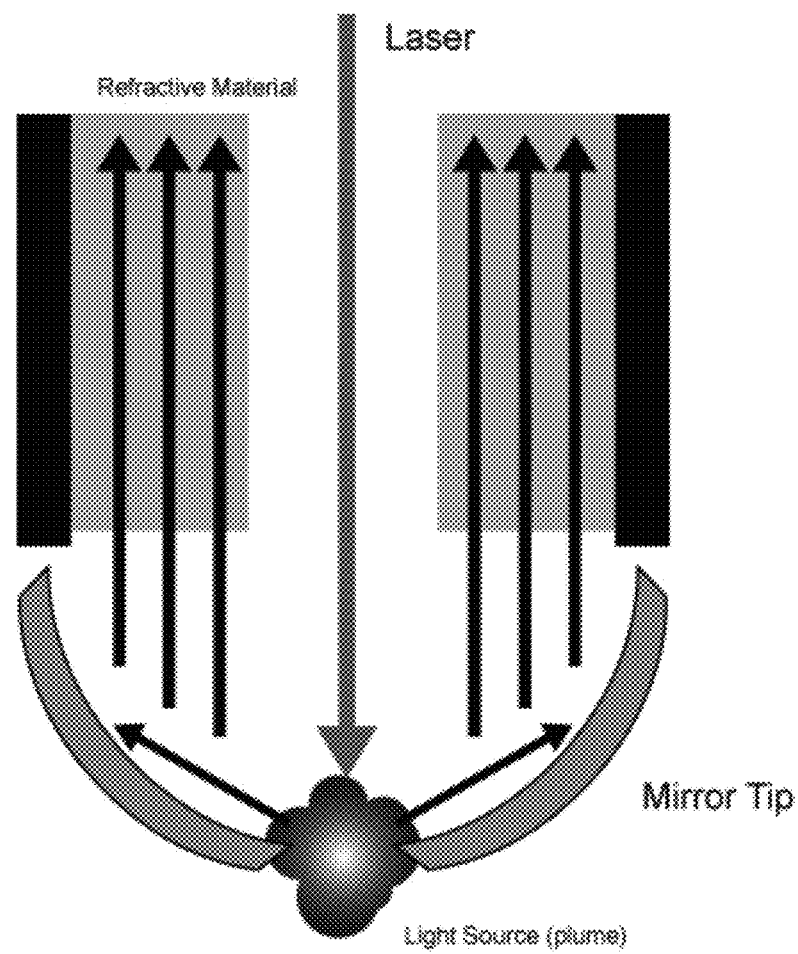
FIG. 11 is a drawing showing an exemplary light pipe which transports light from the tip according to some embodiments.
Figure 12:
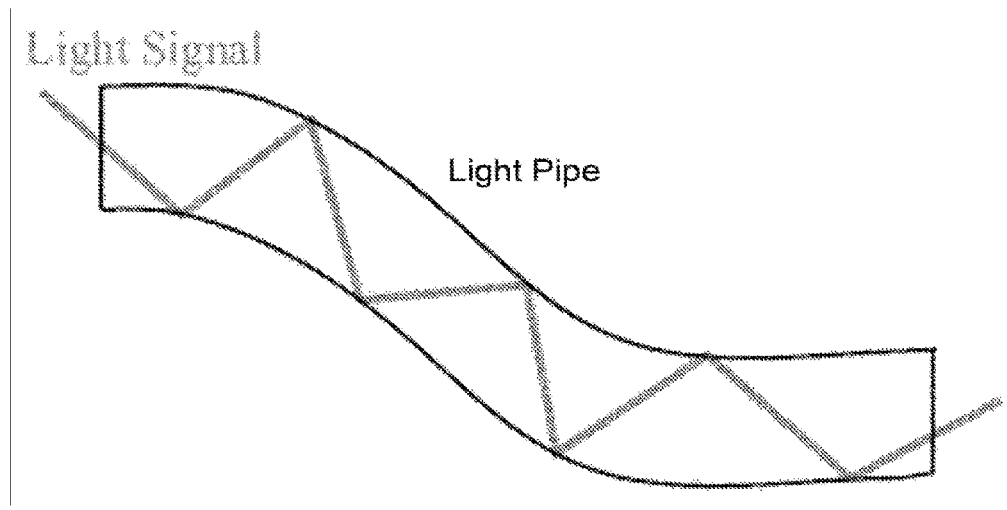
FIG. 12 is a drawing showing the principle of total internal reflection for use in some embodiments.
Figure 13:
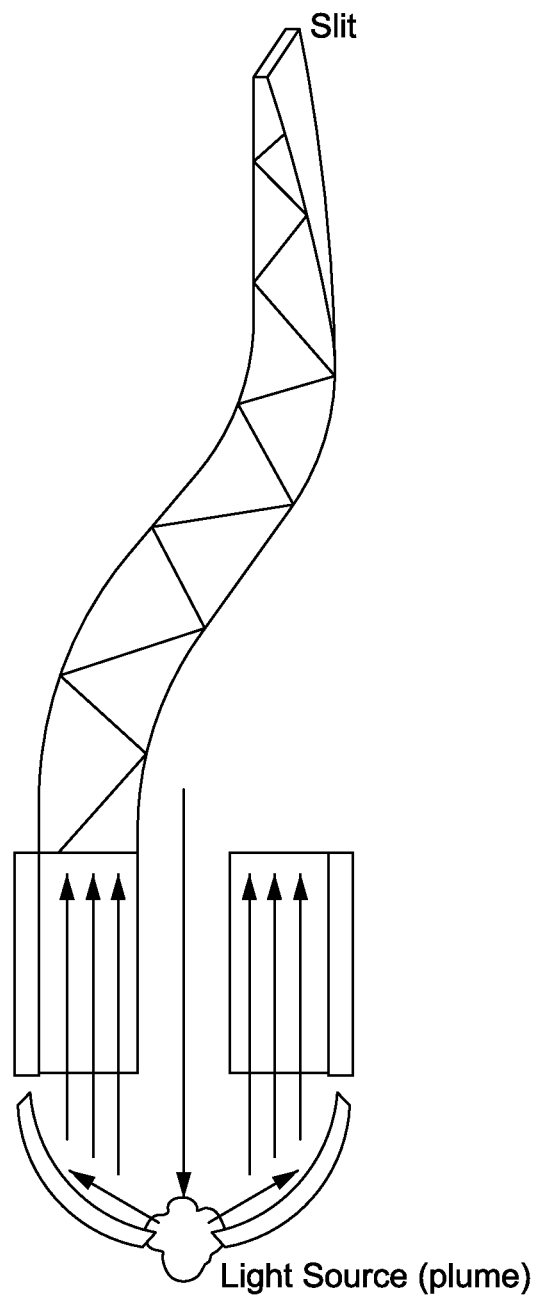
FIG. 13 is a drawing showing an exemplary light pipe which terminates in a slit according to some embodiments.
Figure 14:
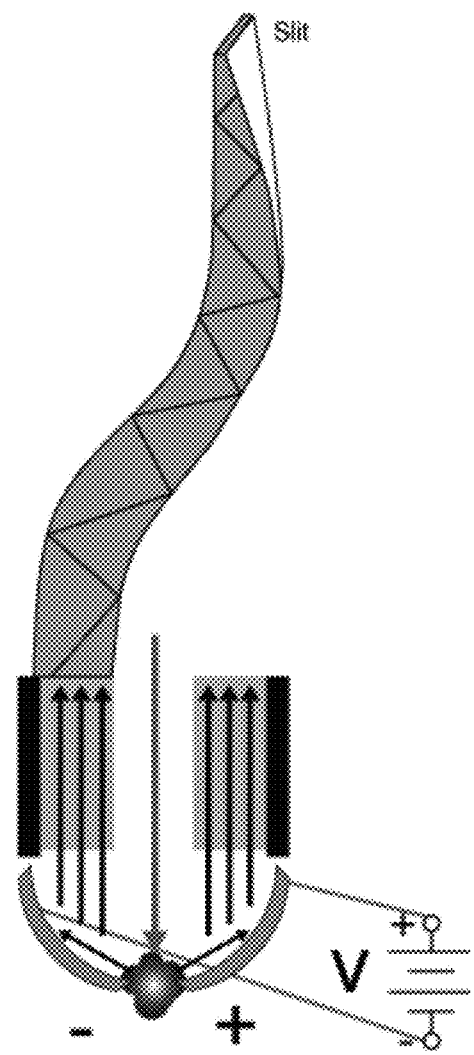
FIG. 14 is a drawing showing an exemplary system with ionization potential added.

In one embodiment, the system utilizes a disposable target tip such as that shown in FIG. 6. In the case where SSS is employed, the tip can simply be two pieces of metal such as zinc which is shown in FIG. 7 as part of a lead-only detection device. In the case where LIBS (such as that shown in FIG. 8 and FIG. 9) or SSS (such as that shown in FIG. 7) or LAES spectroscopy is employed, the interior of the tip will build up deposits over repeated samples ultimately attenuating the light level. Permitting the tip to be replaced by the end user permits a longer useful life for the device.

In one embodiment where the means is SSS, the read head can be separated from the spark generator. For example, a conventional electric fence charger may be used which can be plugged into the wall attached via a flexible power cable to the read head. Similarly the head can be connected via a fiberoptic feed to the spectroscopic and electronics package which is also separated from the read head. Such an embodiment permits continuous use of the device without battery recharge permitting readings at a high rate such as one every second yet permitting many readings over a short period of time. Similarly in a manufacturing setting a similar design can be used for any spectroscopic means which permits high speed readings which are fed into the manufacturing process to indicate if parts being produced are free of toxins.

In one embodiment, safety factors are embedded in the device that enable appropriate safety mechanisms that prevent discharge of the device if the target is inappropriate. For example, a thermal sensor directed at the target can determine if the target temperature is in the range of a living being, and prevent the firing of the spectrum inducing system if the temperature is in a risk range. Further, the system can be designed with a key locking system that must be enabled prior to use of the unit. Further, a mechanical interlock device is envisioned that ensures that the device is physically positioned on the target, thereby preventing firing of the spectrum inducing system into free air or at a distant target. Further, a proximity sensor is envisioned that ensures that the mechanical interlock has not been defeated or broken, again ensuring that the device is proximate to a target preventing firing of the spectrum inducing system into free air or at a distant target. Further an optical interruption system is envisioned that prevents firing of the system in the event that an object is placed into the tip of the device breaking a light stream.

In some embodiment of the invention, we can also increase the collection of light, transport the light, and shape the collected light into a slit which through the combination of design effects can increase the light available to the spectrometer by a factor of 2-3 over other means of light collection as exemplified in FIGS. 10-14.

Figure 15:
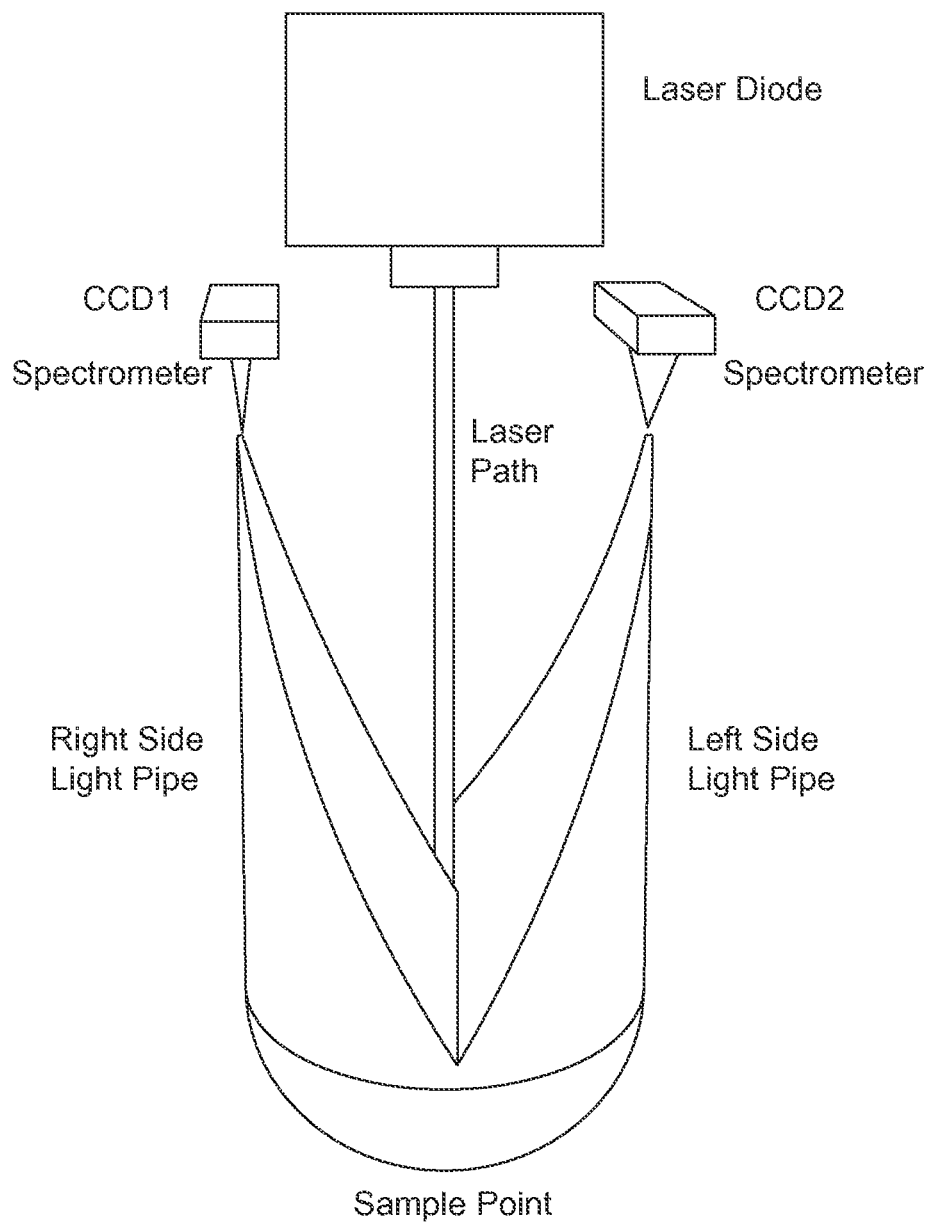
FIG. 15 is a CAD layout of an exemplary LIBS head.
Figure 16:
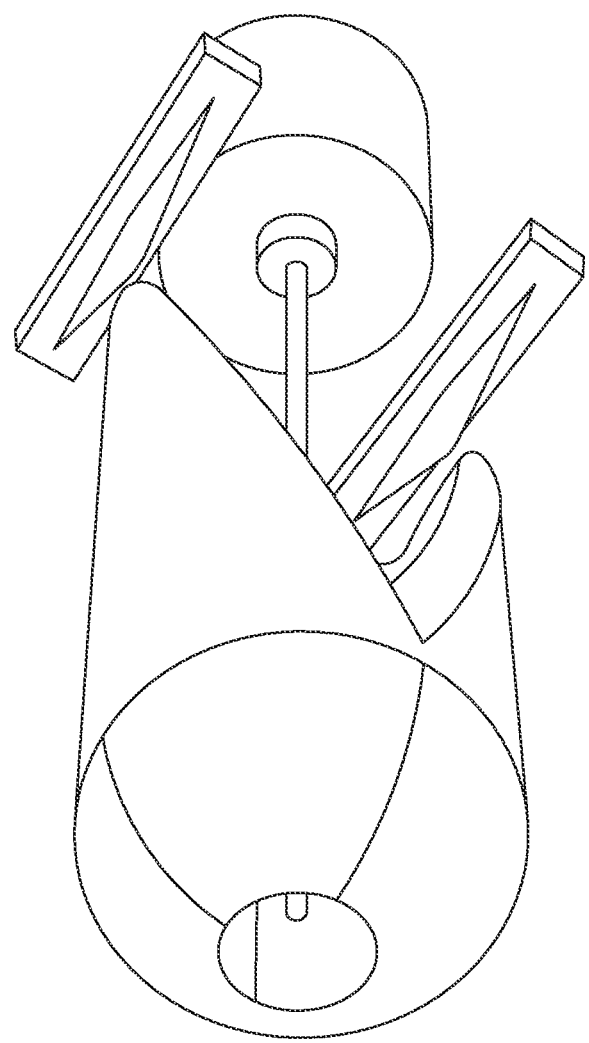
FIG. 16 is an alternative view of FIG. 15.

In one embodiment, the first stage of the system consists of a tip which surrounds the LIBS target. At or near contact with the sample, the end of the tip consists of an outer mirrored surface that redirects the light emitted by the plume into a single direction. In a perfect setting just under 50% of the available light would be reflected upwards towards the light pipe above. The balance of the light is lost because it is emitted below the plane of the reflector and can be presumed to be absorbed by the sample surface. A small further region of loss is through the central portion of the tip through which the laser is fired since no optical controls are available along that path. This can be compared to fiber bundle placed at one side of the plume which at best can collect just under 25% of the available light. Practicalities in placing the bundle require that it be offset from the plume by several 10s of microns which reduces the total light collection potential to 15 to 20% of the available light. Through our design, a factor of 2 to 3 increase in light collection can be routinely expected as illustrated in FIGS. 15 and 16.

The second stage of the system consists of a conventional light pipe fabricated from a refractive material such as glass or acrylic. Light pipe designs typically consists of total internal reflection designs where in the material has a refractive index on the order of 1.4 and the material air boundary interface forces total internal reflection and the transport of light through the pipe at high efficiency. Some light loss occurs in transport, typically on the order of 10%, but this can be reduced by careful selection of materials, management of material purity, and fine polish of the air or cladding boundary as is common in most fiber optic cable designs.

The combination of these two elements results in a system design that collects and transports light into what would be, in one embodiment, a structure resembling a hollow tube, the center of which permits the emission initiator to impact the sample surface through the center of the tube.

In one embodiment, a third element of light pipe design comes into play. Provided the cladding interface is sufficiently smooth, the light pipe can be bent or otherwise shaped arbitrarily which permits the light transport to be adjusted into any relatively arbitrary shape. In one embodiment, the pipe is gradually deformed from a cylinder into one or more linear slits which are sized at their end to match the slit size common to spectroscopy. Various slit sizes can be shaped in this way, for example, 50 or 100 micron slits. Similarly, if the cylinder and tip structure is bifurcated such that there are two half cylinders with corresponding mirror surfaces, two slits can be derived, one for each half cylinder, thus permitting multiple types of spectroscopy to be performed, i.e., a broad band spectrograph and a narrow band spectrograph. In a further embodiment, any number of partial cylinders, 3, 4, etc., can be formed together permitting an arbitrary number of broad and narrow band spectra to be collected from the single light collection device.

In a further embodiment, the mirror material can be a conductive material, such as Aluminum. If there is, for example, a bifurcated cylinder consisting of two half cylinders to compose the single tip, and if there is electrical isolation between the two halves, and if we create an electric potential by connecting wires to each of the opposing mirror elements connected to a power supply providing a voltage differential between the two halves, then an electric field can be delivered to the region surrounding the LIBS induced plume. In such a case, the tip not only collects the light, but the electric field can enhance the plume ionization and further increase the light output of the plume for spectrographic analysis.

In a further embodiment, in addition to or in place of delivering the electric potential field, the tip can measure the resistance of the material surface. In such a case, it would be possible to determine if the resistance were in the range of living tissue resistance then the firing of the laser could be inhibited for safety concerns.

In a further embodiment, it can be anticipated that over time, plume residue will build up on the inside of the device near the plume reducing the transmission efficiency of light into the system. In such a case, the tip nearest the plume, or the entire device can be manufactured in such a way that it can be replaced as a module with an equivalent device.

In a further embodiment, it is possible to have one or more light sources internal to the system which propagate light back into the system. For example, it may be desirable to provide an operation with an indication the system is ready to initiate the plume. As a safety feature, for example an internal LED that is illuminated (for example blue) may be used to indicate that the initiating laser is disabled, and, for example, an internal LED that is illuminated (for example red) may be used to indicate that the initiating laser is ready to fire. This permits a visual safety indicator to the person operating the system. In like fashion alternative embodiments can select to employ auditory, tactile, mechanical, machine communications, electronic, or time-limiting features that provide a selection of notifications, inhibiting interlocks, enabling interlocks, or informational indicators as the work environment of the embodiment applies a need.

In one embodiment, the device is powered by onboard rechargeable or disposable batteries. The device may be powered from standard plug-in sources as well.

In one embodiment, the device itself is fabricated from bio-degradable and/or non-toxic materials so that the device itself does not contribute to the problems it is designed to detect.

In one embodiment, an indicator displays the safety of the sample as follows: Green light indicates safe. Yellow light indicates caution. Red light indicates levels above permissible levels. In the case where multiple substances are tested simultaneously, a small visual or auditory output such as an LED or tone can indicate the substance with a corresponding green/yellow/red coloration or tonal variation.

Exemplary Embodiments

Figure 17:
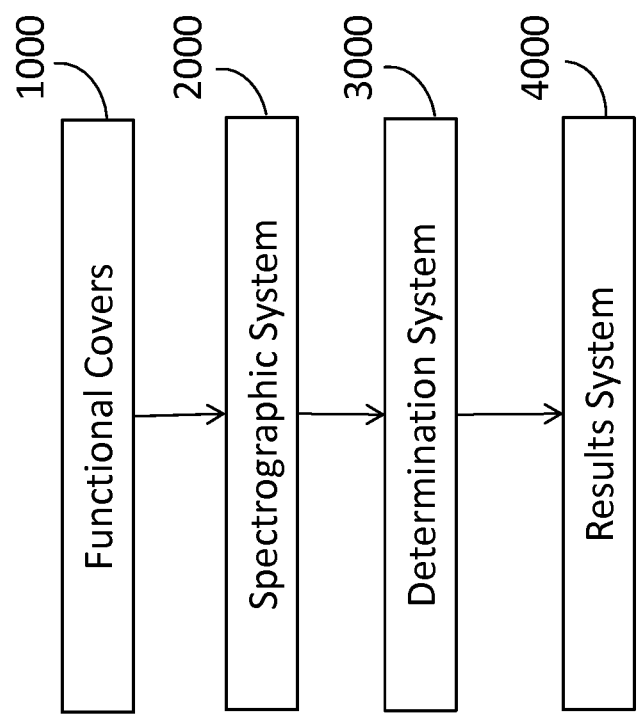
FIG. 17 is block diagram illustrating components of an exemplary toxicity testing device.

FIG. 17 is a block diagram illustrating components of an exemplary toxicity testing device for use with embodiments of the invention. As shown at FIG. 17, a toxicity testing device may include functional covers (1000), a spectroscopic system (2000), a determination system (3000) and a results system (4000).

Functional covers 1000 may include plurality of mechanisms, static or dynamic design elements, or packaging elements to implement functions to improve usability, durability, flexibility, or capability. The Functional Covers (1000) function to a plurality of restriction, concentration, or isolation for the Spectroscopic System (2000). An embodiment that illustrates restriction is a plastic or quartz cover that protects the Spectroscopic System (2000) by restricting harmful environmental conditions such as heat or debris from damaging the Spectroscopic System (2000) and thus the Functional Cover (1000) improves durability. An embodiment that illustrates concentration is a focusing lens, sound concentrator, or enhanced antenna that increases the intensity of the physical phenomena and thereby improves the usability of the apparatus. An embodiment that illustrates isolation is a shutter mechanism that isolates a time interval for the Spectroscopic System (2000) to perform thereby improving the flexibility and capability of the apparatus to perform in extreme conditions. The Functional Covers (1000) in an alternative embodiment can provide a plurality of safety, ambient, or contextual sensors for data and measurement outputs to be processed by the Determination System (3000) or to control the apparatus.

The embodiments of the Spectroscopic System (2000) may include a plurality of apparatus and functions to Collector (2100) the physical phenomena to a plurality of Filters (2200) and then to Detectors (2300) and then to Transport (2400). The plurality of isolating, reducing, amplifying, or other transformations that occur in Filters (2200) function to isolating (illustrated as restrict measurement outputs to narrow measurement), reduce (illustrated by selecting for significant data from a set across events), amplify (illustrated by scaling data), or transform (illustrated by conversion from a light to electrical current). The Transport (2300) function to transport the physical filtering measurement outputs (from Filters (2200)) to the Detectors (2400). The Transport (2300) may perform a plurality of effects that degrade, enhance, or transform the physical filtering measurement outputs prior to the Detectors (2400). The Detectors (2400) embodiments comprise a plurality of detection devices that can be arranged as a single point of detection, a logical distribution of detection, or a complex distribution and sequence of detection. The Detectors (2400) embodiments may be a simple device that converts light to electricity, or a complex device that employs electronics to transform the physical filtering measurement outputs to an analog, digital, or physical output. In a trivial embodiment a Detector (2400) could be used to trigger the release of a ping pong ball into a basket based on the detection of a physical filtering measurement output that was sufficient to trip a switch providing an electro-mechanical output. In another alternative embodiment the Detector (2400) may produce an analog output of a varying voltage or current. In another alternative embodiment the Detector (2400) may produce a digital value from the conversion of the physical filtering measurement output to be passed to the Determination System (3000).

The embodiments of Determination System (3000) may include a plurality of elements that process, evaluate, or transform the measurement outputs from the Functional Covers (1000) or Spectrographic System (2000) to determine a plurality of presence, absence, prevalence, or data. In a very simple embodiment an analog voltage produced from the Spectroscopic System (IB-2400) is transformed by the Determination System (3000) in the form of movement on an analog meter arm. The library of known results for a toxic is represented by a movement of the analog meter arm. (IC-3100). The prevalence of the toxic under test is represented by the rate of change of position of the analog meter arm and the degree of sweep of the analog meter arm. (IC-3200) The value representing the presence or absence result may be determined from the calibrated gradations on the analog meter dial (with thresholds for toxicity illustrated by shading or lines on the analog meter dial). (IC-3300). The value representing prevalence of the toxic may be determined by retaining the maximum sweep position for the analog meter arm and then using a calibrated gradations on the analog meter dial (IC-3400). In similar fashion, an alternative embodiment could also use a tonal audio output with a rising audible frequency in analogous place to the analog meter arm. In this alternative embodiment the audio output does not require any computer processor to achieve a functional result with the alternative embodiment apparatus. The presence of a toxic and thresholds can be matched to audible perceptible frequency and sound levels using just the analog current output from the Spectroscopic System (IB-2400) transformed to a speaker. (IC-3100) The prevalence of the toxic can be evaluated using the volume of the sound. (IC-3200). The value representing presence or absence can be determined from the frequency of the tone. (IC-3300) The value representing the prevalence of a toxic can be determined from the sustained sound level or time for sound level changes that are perceptible. (IC-3400).

In one embodiment, the measurement outputs of the Spectroscopic System (IB-2400) is processed and evaluated by a computational element (IC-3100) to compare with a stored digital library to determine presence of a toxic. The processing of the measurement outputs of the Spectroscopic System (IB-2400) to determine prevalence of the toxic (IC-3200) uses stored digital information to compute prevalence information. The transformation of the measurement outputs of the Spectroscopic System (IB-2400) to presence information uses an algorithm to normalize the representation (IC-3300). The transformation of the measurement outputs of the Spectroscopic System (IB-2400) to a prevalence information uses an algorithm to normalize the representation (IC-3400).

In some embodiments, a plurality of functions (IC-3100, IC-3200, IC-3300, IC-3400) can be applied to a plurality of multiple events, multiple outputs from the Spectroscopic System (IB-2400) for a plurality of multiple toxics, or for more complex processing, evaluation, or transformations.

In some embodiments, the apparatus can acquire contextual or ambient data (IA-1000, IB-2000) for processing by the Determination System (IC-3000) and the output thru the Results system (ID-4000).

The Results System (4000) may report, display, or Store the determination from the Determination System (3000) for use by people or other apparatus. In some embodiments, the reporting or displaying of the determinations may transform the presence and prevalence data from the Determination System (3000) into forms, media, and formats useful to people or other apparatus. The Store function of Results System (4000) may communicate outputs of the Determination system (3000) in a plurality of forms, media, and formats to capacities to store data, transmissions to other apparatus, or to retain a persistent representation (illustrated by a hazard light retained until reset).

In one embodiment, the results may be reported and displayed on a plurality of LED displays, tonal audible outputs, vibration, and stored in a digital storage capacity such as an SD Card. In alternative embodiments the apparatus may have a plurality of features to enhance reports, displays, and storage capabilities to perform in a wide variety of toxic testing environments where there may be multiple events, multiple operators, multiple tests, or interconnections.

Toxicity Testing devices may include different categories or classes of devices. For example, the Toxicity Testing devices may be categorized or classified based on a common characteristic (among multiple characteristics that are common or uncommon) of the steps subsequent to actions of the Spectroscopic System (2000). The first class (Class I below) handles a plurality of the outcomes from the Spectroscopic System (2000) as measurement outputs that are a plurality of output measurements for specific subsets of spectra. The second class (Class II below) handles a plurality of the outcomes from the Spectroscopic System (2000) as sets (including subsets) of spectra.

Functional covers (1000), a spectroscopic system (2000), a determination system (3000) and a results system (4000) are referenced for Spectrographic System (2000) Class I and Class II embodiments and apparatus. Common to Class I and Class II embodiments are testing processes that cover 'events' that may last for a single finite interval (a 'snapshot' of a fraction of a second in a possible embodiment), a longer finite interval (an 'exposure' of a duration of time in a possible embodiment), a continuous period (a 'continuous reading'), or a series of 'events' (single, longer, continuous, intermittent, occasional) where the Determination System (3000) and the Results System (4000) may perform a plurality of functions that acquire, collect, process, evaluate, transform, display, report, store, compare, analyze, assess, compile, isolate, or synthesize; from the outcomes and measurements of testing processes' events. In a preferred embodiment the acquisition of outcomes is accomplished by the Functional Covers (1000) and Spectroscopic System (2000). The collection, process, evaluate and transform processes are accomplished in a preferred embodiment by the Spectroscopic System (2000) and the Determination System (3000). The plurality of functions to display, report, store, compare, analyze, assess, compile, isolate, or synthesize from the outcomes and measurements are accomplished in a preferred embodiment by the Determination System (3000) and the Results System (4000). A plurality of the functions are present in embodiments to compare (to control cases, library cases, stored results, and between or during events), analyze (perform mathematical and logical operations including considering stored information, standards, or static or dynamic rules), assess (determine according to conformance to stated or generated guides and rules), compile (accumulate, consolidate, reduce, or extend the existence of multiple data), isolate (reduce by selection, select by static or dynamic rule, select by temporal rule, select by chance), or synthesize (creating a result based on a plurality of multiple data sources within, or without, of the physical device and apparatus using logic, rules, algorithms, or processes).

An exemplary embodiment comprising a selection of elements for a lead detector may include:

Functional Cover (1000)
An optically transparent plastic or quartz cover that protects the elements of the Spectrographic System (2000) from damage in the measurement process. The cover in an exemplary embodiment is replaceable and exchangeable.

Spectrographic System (2000)
Comprising a collection of elements that perform Collection (2100) started by actions of the measurement process, Filter (2200) using optical wavelength filters to isolate to the light and intensity of interest (from 1000), Transport (2300) using a fiber optical cable to a Detector (2400) that uses a CCD device to create an outcome measurement of intensity.

Determination System (3000)
Comprising a collection of elements that perform a plurality of functions process, evaluate, and transform (3100, 3200, 3300, 3400) the outcome measurement of intensity (from 2000) to a plurality of determination, prevalence, and values.

Results System (4000)
Comprising a collection of elements that perform a plurality of functions to display, report, or store (4000) the results of the Determination System (3000) by an LED display, indicator lights, audible tones, vibration, and communications to a store.

In one embodiment, the testing device may be a class I testing device for testing materials for toxics comprising: (IA-1000)

A) A plurality of zero or more mechanical, optical, shaped materials, or logical covers that restrict, concentrate, or isolate a plurality of one or more wavelengths of electromagnetic radiation, quantum effects, or acoustic outcomes for the spectroscopic system or other measurement B) a spectroscopic system for measuring substances, the spectroscopic system comprising: (IB-2000, IB-2100, IB-2200, IB-2300, IB-2400)
- B1) a collection mechanism that is exposes the physical phenomena from zero or more emission events to a plurality of one or more physical filtering elements, (IB-2100)
- B2) a plurality of one or more physical filtering elements that selectively apply a function to a plurality of one or more wavelengths of electromagnetic radiation, quantum effects, or acoustic outcomes where each physical filtering elements consist of one or more mechanical or logical arrangements where the geometric, topological, quantity, or sequencing arrangement serves a function to produce a desired output (the physical filtering element outputs) by isolating, reducing, amplifying, or other transformations of the wavelengths of electromagnetic radiation, quantum effects, or acoustic outcomes, (IB-2200)
- B3) a transport of the physical filtering element outputs to detection or processing apparatus, (IB-2300)
- B4) a detection or processing apparatus that produces an analog, digital, or physical output measurement representation (the measurement output) from the incoming physical filtering element outputs where the detection or processing apparatus is mechanically or logically arranged as a plurality of a single, multiple, or complex grouping of mechanical, acoustic, electromagnetic radiation, electronic, or quantum processing devices, (IB-2400)

C) A processing or evaluation or transformation that produces a plurality of the outcomes of: (IC-3000)
- C1) the measurement outputs of the spectroscopic system are processed by the apparatus to evaluate the presence or absence of toxic substance against a known library of emission measurements and then display, report, or store the presence status (IC-3100)
- C2) the measurement outputs of the spectroscopic system are processed by the apparatus to evaluate the presence or absence of toxic substance against a known library of emission measurements and then display, report, or store the prevalence information (IC-3200)
- C3) the measurement outputs of the spectroscopic system is processed by the apparatus to collect representations of measurement outputs and then display, report, or store the measurement values of the filtered output measurement (IC-3300)
- C4) the measurement outputs of the spectroscopic system is processed by the apparatus to collect representations of measurement outputs and then display, report, or store the measurement values of the filtered output measurement for prevalence (IC-3400)

D) Display, report, or storage elements that provide a plurality of functions for visual, tactile, audible, or electronic transmission notifications of measurements of presence or absence of substances; store and recall values; (ID-4000)

In one embodiment, the testing device may be a class II testing device for testing materials for toxics comprising:
A) A plurality of zero or more mechanical, optical, shaped materials, or logical covers that restrict, concentrate, or isolate a plurality of one or more wavelengths of electromagnetic radiation, quantum effects, or acoustic outcomes for the spectroscopic system or other measurement (IIA-1000)

B) a spectroscopic system for measuring substances, the spectroscopic system comprising: (IIB-2000, IIB-2100, IIB-2200, IIB-2300, IIB-2400)
- B1) a collection mechanism that is exposes the physical phenomena from zero or more emission events to a plurality of one or more physical filtering elements, (IIB-2100)
- B2) a plurality of one or more physical filtering elements that selectively apply a function to a plurality of one or more wavelengths of electromagnetic radiation, quantum effects, or acoustic outcomes where each physical filtering elements consist of one or more mechanical or logical arrangements where the geometric, topological, quantity, or sequencing arrangement serves a function to produce a desired output spectra (the physical filtering element spectra outputs) by isolating, reducing, amplifying, or other transformations of the wavelengths of electromagnetic radiation, quantum effects, or acoustic outcomes, (IIB-2200)
- B3) a transport of the physical filtering element output spectra to detection or processing apparatus, (IIB-2300)
- B4) a detection or processing apparatus that produces an analog, digital, or physical output measurement value or values (the measurement output spectra) in digital representation from the incoming physical filtering element output spectra where the detection or processing apparatus is mechanically or logically arranged as a plurality of a single, multiple, or complex grouping of mechanical, acoustic, electro-magnetic radiation, electronic, or quantum processing devices, (IIB-2400)

C) A processing or evaluation or transformation processed using a numerical process computed using a conventional PLDA statistical model or equivalent, assigns a categorical classification to one or more of the substance, or substances, determines if the substance, or substances, were present or absent, and compares the categorical classification of the substance to a known library of spectra, that produces a plurality of the outcomes for zero or more substances of: (IIC-3000, IIC-3100, IIC-3200, IIC-3300, IIC-3400)
- C1) the measurement outputs of the spectroscopic system are processed by the apparatus to evaluate the presence or absence of toxic substance against a known library of emission measurements and then display, report, or store the presence status (IIC-3100)
- C2) the measurement outputs of the spectroscopic system are processed by the apparatus to evaluate the presence or absence of toxic substance against a known library of emission measurements and then display, report, or store the prevalence information (IIC-3200)
- C3) the measurement outputs of the spectroscopic system is processed by the apparatus to collect representations of measurement outputs and then display, report, or store the measurement values of the filtered output measurement (IIC-3300)
- C4) the measurement outputs of the spectroscopic system is processed by the apparatus to collect representations of measurement outputs and then display, report, or store the measurement values of the filtered output measurement for prevalence (IIC-3400)

D) Display, report, or storage elements that provide a plurality of functions for visual, tactile, audible, or electronic transmission notifications of measurements of presence or absence of substances; store and recall values; (IID-4000)

Table 1 below illustrates embodiments of the invention.

TABLE 1

| Embodiment Elements | Function | Input | Output | Embodiment Example |
|---|---|---|---|---|
| IA Functional Covers (1000) | restrict, concentrate, or isolate | Ambient phenomena | Ambient phenomena | Physical slit Parabolic reflector Physical 'camera shutter' |
| IB Spectrographic System (2000) | Spectrographic System | | | |
| IB1 Collector (2100) | Collection mechanism | Events or stream of events | Division of event or passage of a stream of events | |
| IB2 Filter (2200) | Filtering | wavelengths of electromagnetic radiation, quantum effects, or acoustic outcomes | physical filtering element outputs produced by isolating, reducing, amplifying, or other transformations | Radio frequency filter optical wavelength isolator acoustic barrier |
| IB3 Transport (2300) | Transport | physical filtering element outputs | Physical filtering element outputs (may be transformed by transport) | Radio waveguide optical fiber sound tube |
| IB4 Detector (2400) | Detection or Processing | physical filtering element outputs | analog, digital, or physical output measurement representation (the measurement output) | Voltage −5 to 5 v numeric values Physical objects |
| IC (3000) Determination System | Processing or evaluation or transformation | Measurement Output Library and processing parameters | Determination or representation | Direct chemical or analogue processing (light from reactive chemicals) Library of toxics |
| IC1 Determine Presence (3100) | Make Determination of Presence | measurement outputs of the spectroscopic system | Presence or absence determination | Lead is present Arsenic is absent |
| IC2 Determine Prevalence (3200) | Make Determination of Prevalence | measurement outputs of the spectroscopic system | Prevalence determination | Less than 10 ppm More than 1% |
| IC3 Determine Presence Value (3300) | Represent Presence Value | measurement outputs of the spectroscopic system | Presence or absence value representation | Lead is present in 2 of 10 events at a level of 100 ppm, 200 ppm |
| IC4 Determine Prevalence Value (3400) | Represent Prevalence Value | measurement outputs of the spectroscopic system | Prevalence value representation | 2 of 12 events have lead prevalent at more than 500 ppm |
| ID Results System (4000) | Display, report, or storage | Presence data, prevalence data, transformation rules for notifications | visual, tactile, audible, or electronic transmission | "Red Light" or "Green Light" Vibration/haptic feedback Audible tone(s) Communications media message such as a text message Stored data on SD Card |
| IIA Functional Covers (1000) | restrict, concentrate, or isolate | Ambient phenomena | Ambient phenomena | Physical slit Parabolic reflector Physical 'camera shutter' |
| IIB Spectrographic System (2000) | Spectrographic System | | | |
| IIB1 Collector (2100) | collection mechanism | Events or stream of events | Division of event or passage of a stream of events | |

TABLE 1-continued

| Embodiment Elements | Function | Input | Output | Embodiment Example |
|---|---|---|---|---|
| IIB2 Filter (2200) | Filtering | wavelengths of electromagnetic radiation, quantum effects, or acoustic outcomes | physical filtering element produces desired output spectra (the physical filtering element spectra outputs) by isolating, reducing, amplifying, or other transformations | Radio spectra optical spectra acoustic spectra |
| IIB3 Transport (2300) | Transport | physical filtering element output spectra | Physical filtering element output spectra (may be transformed by transport) | Radio waveguide optical multimode fiber sound tube |
| IIB4 Detector (2400) | Detection or Processing | physical filtering element outputs | analog, digital, or physical output measurement value or values (the measurement output spectra) in digital representation | Numeric values |
| IIC Determination System (3000) | Processing or evaluation or transformation | Digital representation of spectra Library and processing parameters | Determination or representation | Film spectra output Frequency spectrum plot |
| IIC1 Determine Presence (3100) | Make Determination of Presence | measurement outputs of the spectroscopic system | Presence or absence determination | Lead is present Arsenic is absent |
| IIC2 Determine Prevalence (3200) | Make Determination of Prevalence | measurement outputs of the spectroscopic system | Prevalence determination | Less than 10 ppm More than 1% |
| IIC3 Determine Presence Value (3300) | Represent Presence Value | measurement outputs of the spectroscopic system | Presence or absence value representation | Lead is present in 2 of 10 events at a level of 100 ppm, 200 ppm |
| IIC4 Determine Prevalence Value (3400) | Represent Prevalence Value | measurement outputs of the spectroscopic system | Prevalence value representation | 2 of 12 events have lead prevalent at more than 500 ppm |
| IID Results System (4000) | Display, report, or storage | Presence data, prevalence data, transformation rules for notifications | visual, tactile, audible, or electronic transmission | "Red Light" or "Green Light" Vibration/haptic feedback Audible tone(s) Communications media message such as a text message Stored data on SD Card |

Embodiments have been described herein. Those skilled in the art will appreciate that various modifications and substitutions are possible, without departing from the scope of the invention as claimed and disclosed, including the full scope of equivalents thereof

What is claimed is:

1. A toxin detector comprising:
   a spectroscopic system for analyzing a sample, the spectroscopic system comprising:
      one or more collectors for collecting physical phenomena from one or more emission events associated with the sample;
      one or more filters for filtering the physical phenomena from the one or more collectors by one or more of isolating, reducing, amplifying, or sequencing the physical phenomena into a filtered spectra output;
      one or more detectors for receiving the filtered spectra output and producing one or more output measurement values;
      one or more transporters for transporting the filtered spectra output from the one or more filters to the one or more detectors;
   a determination system for processing the one or more output measurement values of the spectroscopic system, the determination system comprising a processor configured to perform one or more of:
      evaluating the presence or absence of a toxin against a known library of emission measurements;
      evaluating the prevalence of a toxin against a known library of emission measurements;
      collecting representations of measurement outputs value; and assigning a categorical classification to the one or more toxins based on a Partial Least-Squares Discriminate-Function Analysis (PLDA) statistical analysis of the output measurement value;

wherein the one or more collectors comprise a device that captures light comprising a central region through which an atomic or molecular emission initiation means is propagated, and a surrounding optical structure which directs emitted light in a uniform direction;

wherein the optical structure is a concave mirror;

wherein the concave mirror is the exterior sheath of a light pipe which conducts light via internal reflection; and wherein the light pipe is reduced at an end opposite the collector to one or more small rectangular region(s) optically equivalent to a spectroscopic slit.

2. The toxin detector according to claim 1, further comprising:

a results system configured to one or more of display, report, and store one or more of the output measurement value, presence or absence of the one or more toxins, the prevalence of the one or more toxins, the collected representations of the measurement output value, and the assigned categorical classification of the one or more toxins.

3. The toxin detector according to claim 1, further comprising:

one or more functional covers configured to restrict, concentrate or isolate effects entering the spectroscopy system.

4. The toxin detector according to claim 1, wherein the spectroscopy system is configured to measure at least one of acoustic, quantum, optical, or radio spectra produced by one or more of: laser induced breakdown spectroscopy, Raman spectroscopy, X-ray florescence spectroscopy, reflectance spectroscopy, acoustic spectroscopy, and radio spectroscopy.

5. The toxin detector according to claim 1, wherein the mirror is electrically conductive and bifurcated in a manner that electrically isolates each portion.

6. The toxin detector according to claim 5, wherein each bifurcated portion of the mirror is connected to an electric potential.

7. The toxin detector according to claim 6, wherein the electric potential is used to enhance the ionization of the atomic or molecular emission.

8. The toxin detector according to claim 5, wherein either electrical conductivity or capacitance can be measured.

9. The toxin detector according to claim 8, wherein the measurement is used as a safety feature to permit or inhibit emission initiation.

10. The toxin detector according to claim 1, wherein the light pipe is shaped to direct the captured light to one or more detectors.

11. The toxin detector according to claim 1, wherein the light pipe is reduced at an end opposite the collector to one or more small region(s) which can be directly imaged.

12. The toxin detector according to claim 1, wherein the physical phenomena is one or more spectra and the one or more transporters comprise one or more light pipe.

13. The toxin detector of claim 12, wherein the light pipe defines two or more regions independently selected from a spectroscopic slit, and a region capable of being directly imaged.

14. The toxin detector according to claim 12, wherein the light pipe is sheathed in a cladding that enhances the internal reflection efficiency.

15. The toxin detector according to claim 1, wherein the one or more filters comprise one or more of optical bandpass filters and waveguide gratings wherein each is configured to pass a specific persistent emission line characteristic of the one or more toxins.

16. The toxin detector according to claim 15, wherein the one or more filters are arranged as a vector or an array.

17. The toxin detector of claim 1, wherein the one or more detectors comprise one or more charge coupled device (CCD).

18. The toxin detector of claim 1, wherein the determination system comprises a processor configured to compare the magnitude of a detected spectrum against a library of known detected spectra of the one or more toxin.

19. The toxin detector of claim 1, wherein the determination system comprises a processor configured to employ Partial Least-Squares Derivative-Functional Analysis (PLDA) statistical models to assign a categorical classification to determine the presence of the one or more toxin.

20. A device for determining the presence of one or more toxins, the device comprising:

a spectroscopy system comprising:

a light source selected from at least one of: Laser Induced Breakdown Spectroscopy (LIBS), Sliding Spark spectroscopy (SSS), Raman spectroscopy, Laser Ablation Emission Spectroscopy (LAES), X-Ray Fluorescence spectroscopy (XRF), and reflectance spectroscopy;

an electromagnetic measurement device;

one or more collectors for collecting physical phenomena from the light source;

one or more filtering elements configured to filter the physical phenomena from the light source and pass one or more specific persistent emission lines associated with the one or more toxins to the electromagnetic measurement device;

wherein the one or more collectors and the one or more filtering elements are positioned between the spectroscopy system and the electromagnetic measurement device; and a processor configured to receive data from the electromagnetic measurement device and to determine the presence of the one or more toxins;

wherein the one or more collectors comprise a device that captures light comprising a central region through which an atomic or molecular emission initiation means is propagated, and a surrounding optical structure which directs emitted light in a uniform direction;

wherein the optical structure is a concave mirror;

wherein the concave mirror is the exterior sheath of a light pipe which conducts light via internal reflection; and wherein the light pipe is reduced at an end opposite the collector to one or more small rectangular region(s) optically equivalent to a spectroscopic slit.

21. The device according to claim 20, wherein the processor is configured to determine the presence of the one or more toxin by:

a) employing an algorithm to compare the data from the electromagnetic measurement device to a known library containing data associated with the one or more toxins;

b) employing Partial Least-Squares Derivative-Functional Analysis (PLDA) statistical model to assign a categorical classification of the one or more toxin;

c) directly correlating the data from the electromagnetic measurement device to the presence of the one or more toxins; or d) a combination thereof.

22. The device of claim 20, wherein the data from the electromagnetic measurement device is selected from one or more of digitized pixel values, magnitude of a line, magnitude of a line pair, and magnitude of a line triplet.

23. The device of claim 20, wherein the electromagnetic measurement device is a charge coupled device (CCD).

24. The device according to claim 20, wherein the one or more filtering elements are selected from one or more optical bandpass filter or wave guide grating;
   wherein the one or more filtering elements are configured singly, as a vector, or as an array.

25. The device according to claim 20, wherein each of the one or more filtering elements is configured to pass a specific persistent emission line for a specific atomic emission line characteristic of the one or more toxins.

26. The device according to claim 20, wherein the one or more toxins are selected from actinium-227, aluminum, americium, americium-241, antimony, arsenic, barium beryllium bromine, cadmium, cesium-137, chlorine, chromium, chromium (VI) oxide, chromium-hexavalent, cobalt, copper fluorine, iodine-129, iodine-131, lead, lead-210, manganese Mercury, nickel, palladium, white-phosphorus, plutonium, polonium-210, potassium-40, selenium, silver, vanadium, and zinc.

* * * * *